United States Patent
Baker

(10) Patent No.: US 8,676,316 B2
(45) Date of Patent: *Mar. 18, 2014

(54) APPARATUS AND METHOD FOR CALCULATING CALORIC EXPENDITURE USING POSTURE

(75) Inventor: Lemont Baker, Raleigh, NC (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/471,781

(22) Filed: May 15, 2012

(65) Prior Publication Data

US 2012/0226114 A1 Sep. 6, 2012

Related U.S. Application Data

(62) Division of application No. 10/892,937, filed on Jul. 16, 2004, now Pat. No. 8,185,201.

(51) Int. Cl.
*A61N 1/362* (2006.01)

(52) U.S. Cl.
USPC .......................................... 607/19

(58) Field of Classification Search
USPC .......................................... 607/19
See application file for complete search history.

(56) References Cited

U.S. PATENT DOCUMENTS

| | | | |
|---|---|---|---|
| 6,021,352 A | 2/2000 | Christopherson et al. | |
| 6,273,856 B1 * | 8/2001 | Sun et al. | 600/300 |
| 6,539,249 B1 | 3/2003 | Kadhiresan et al. | |
| 6,658,292 B2 | 12/2003 | Kroll et al. | |
| 6,990,375 B2 | 1/2006 | Kloss et al. | |
| 7,260,436 B2 | 8/2007 | Kilgore et al. | |
| 7,328,131 B2 | 2/2008 | Donofrio et al. | |
| 7,844,336 B2 | 11/2010 | Fricke et al. | |
| 8,185,201 B2 * | 5/2012 | Baker | 607/19 |
| 2002/0151936 A1 | 10/2002 | Kloss et al. | |
| 2003/0040776 A1 | 2/2003 | Kroll et al. | |
| 2004/0112151 A1 | 6/2004 | Maxwell et al. | |
| 2004/0127807 A1 | 7/2004 | Hatlestad et al. | |
| 2005/0010265 A1 | 1/2005 | Baru Fassio et al. | |
| 2008/0255626 A1 | 10/2008 | Fricke et al. | |
| 2011/0046520 A1 | 2/2011 | Fricke et al. | |

FOREIGN PATENT DOCUMENTS

| | | |
|---|---|---|
| WO | WO-9502431 A1 | 1/1995 |
| WO | WO-0189365 A2 | 11/2001 |

OTHER PUBLICATIONS

"U.S. Appl. No. 10/892,937, Final Office Action mailed Mar. 11, 2010", 7 pgs.
"U.S. Appl. No. 10/892,937, Final Office Action mailed Aug. 7, 2008", 7 pgs.
"U.S. Appl. No. 10/892,937, Final Office Action mailed Oct. 13, 2011", 6 pgs.

(Continued)

*Primary Examiner* — Eric D. Bertram
(74) *Attorney, Agent, or Firm* — Schwegman Lundberg & Woessner, P.A.

(57) ABSTRACT

Systems and methods for estimating caloric expenditure. The systems can include a physiological sensor to measure a patient's physical activity, and a posture sensor to measure the patient's posture. An estimated caloric expenditure can be calculated based on data from the physiological sensor and the posture sensor. For example, the estimated caloric expenditure can be calculated at least in part based on the posture data. For example, the estimated caloric expenditure can be validated based on the posture data.

13 Claims, 3 Drawing Sheets

(56) References Cited

OTHER PUBLICATIONS

"U.S. Appl. No. 10/892,937, Non Final Office Action mailed Apr. 28, 2011", 6 pgs.
"U.S. Appl. No. 10/892,937, Non-Final Office Action mailed Feb. 3, 2009", 8 pgs.
"U.S. Appl. No. 10/892,937, Non-Final Office Action mailed Feb. 13, 2008", 8 Pgs.
"U.S. Appl. No. 10/892,937, Non-Final Office Action mailed Jul. 19, 2007", 7 pgs.
"U.S. Appl. No. 10/892,937, Notice Of Allowance mailed Jan. 25, 2012", 5 pgs.
"U.S. Appl. No. 10/892,937, Response filed Jan. 13, 2012 to Final Office Action mailed Oct. 13, 2011", 5 pgs.
"U.S. Appl. No. 10/892,937, Response filed May 4, 2009 to Non-Final Office Action mailed Feb. 3, 2009", 7 pgs.
"U.S. Appl. No. 10/892,937, Response filed May 13, 2008 to Non Final Office Action mailed Feb. 13, 2008", 7 pgs.
"U.S. Appl. No. 10/892,937, Response filed Jun. 11, 2010 to Final Office Action mailed Mar. 11, 2010", 6 pgs.
"U.S. Appl. No. 10/892,937, Response filed Aug. 29, 2011 to Non Final Office Action mailed Apr. 28, 2011", 6 pgs.
"U.S. Appl. No. 10/892,937, Response filed Jan. 7, 2009 to Final Office Action mailed Aug. 7, 2008", 7 pgs.
"U.S. Appl. No. 10/892,937, Response filed Nov. 19, 2007 to Non-Final Office Action mailed Jul. 19, 2007", 6 pgs.
"U.S. Appl. No. 10/892,937, Response to Restriction Requirement, filed Sep. 18, 2009", 7 pgs.
"U.S. Appl. No. 10/892,937, Restriction Requirement mailed Aug. 18, 2009", 7 pgs.
"U.S. Appl. No. 11/733,663, Final Office Action mailed May 19, 2010", 8 pgs.
"U.S. Appl. No. 11/733,663, Non-Final Office Action mailed Dec. 10, 2009", 5 pgs.
"U.S. Appl. No. 11/733,663, Notice of Allowance mailed Jul. 23, 2010", 6 pgs.
"U.S. Appl. No. 11/733,663, Response filed Mar. 9, 2010 to Non Final Office Action mailed Dec. 10, 2009", 9 pgs.
"U.S. Appl. No. 11/733,663, Response filed Jun. 22, 2010 to Final Office Action mailed May 19, 2010", 11 pgs.
Arvanitakis, Z., et al., "Diabetes mellitus and progression of rigidity and gait disturbance in older persons", Neurology, 63(6), (2004), 996-1001.
Evangelista, Lorraine S., et al., "Validity of Pedometers for Measuring Exercise Adherence in Heart Failure Patients", Journal of Cardiac Failure, 11(5), (2005), 366-71.
Mancini, D. M., et al., "Value of peak exercise oxygen consumption for optimal timing of cardiac transplantation in ambulatory patients with heart failure", Circulation, 83(3), (1991), 778-86.
Schneider, Patrick L, et al., "Accuracy and reliability of 10 pedometers for measuring steps over a 400-m walk", Medicine and Science in Sports and Exercise, 35(10), (2003), 1779-1784.
Schneider, Patrick L, et al., "Pedometer measures of Free-Living Physical Activity: Comparison of 13 Models", Medicine and Science in Sports and Exercise, 36(2), (2004), 331-335.
Thompson, D. L, et al., "Relationship between Accumulated Walking and body Composition in Middle-Aged Women", Medicine and Science in Sports and Exercise, 36(5), (2004), 911-914.
Walsh, J T, et al., "Relation of daily activity levels in patients with chronic heart failure to long-term prognosis", Am J Cardiol, 79(10), (1997), 1364-1369.

* cited by examiner

APPARATUS AND METHOD FOR CALCULATING CALORIC EXPENDITURE USING POSTURE

CLAIM OF PRIORITY

This application is a division of and claims the benefit of priority under 35 U.S.C. §120 to U.S. patent application Ser. No. 10/892,937, filed on Jul. 16, 2004, now issued as U.S. Pat. No. 8,185,201, which is hereby incorporated by reference herein in its entirety.

TECHNICAL FIELD

The present invention relates to monitoring a patient's metabolic need over time and, more particularly, to estimating and tracking caloric expenditure using sensors associated with cardiac rhythm management devices.

BACKGROUND

A patient's caloric expenditure can provide an estimate of the patient's energy balance and fitness. This measurement can be important for the optimization of therapy provided to patients that have heart problems and require a cardiac rhythm management device such as a pacemaker or a cardiac resynchronization device. For example, caloric expenditure measurements can be used to assess the lifestyle, exertion level, exercise capacity, cardiovascular functional capacity, quality of life, and wellness of a patient for optimization of overall therapy management.

Caloric expenditure is typically measured using the metabolic equivalents (METS) scale. Each MET on the scale corresponds to a multiple of resting caloric expenditure of approximately 3.5 ml/kg/min of oxygen.

There are several known methods for estimating caloric expenditure. One method of estimating caloric expenditure involves indirect calorimetry using cardiopulmonary gas exchange (CPX) variables ($VO_2$, $VCO_2$) of a patient. However, this measurement is difficult to do, particularly outside of a laboratory setting, in that it is necessary to have the patient equipped with respiratory monitoring devices, such as a breathing mask and sample tube, a gas analyzer, ekg leads, and an electronics module for processing the parameters being monitored.

Another method of estimating caloric expenditure is based on the patient's intrinsic heart rate.

For patients that are chronotropically incompetent, other methods for estimating caloric expenditure include use of measurements taken from adaptive rate sensors such as, for example, accelerometers and minute ventilation sensors. For example, U.S. Pat. No. 6,273,856 to Sun et al. describes a method of estimating caloric expenditure using measurements from an accelerometer and minute ventilation sensor used in adaptive rate pacing.

Improvements are needed to methods that allow for estimation of a patient's caloric expenditures during the patient's normal living activity, without requiring difficult, exercise-based CPX measurements.

SUMMARY

The present invention relates to monitoring a patient's metabolic need over time and, more particularly, to estimating and tracking caloric expenditure using sensors associated with cardiac rhythm management devices.

According to one aspect, the invention relates to a cardiac rhythm management device including a physiological sensor producing electrical signals associated with a patient's physical activity and a posture sensor producing electrical signals associated with the patient's posture. The device also includes a controller coupled to the physiological sensor and the posture sensor, the controller calculating an estimated caloric expenditure based on the electrical signals from the physiological sensor and the electrical signals from the posture sensor.

According to another aspect, the invention relates to a method of estimating caloric expenditure, including: implanting in a patient a cardiac rhythm management device including a physiological sensor and a posture sensor; calculating an estimated caloric expenditure based on data provided by the physiological sensor; and validating the estimated caloric expenditure based on data provided by the posture sensor.

According to another aspect, the invention relates to a method of estimating caloric expenditure, including: measuring physical activity; measuring posture; and calculating an estimated caloric expenditure based on measurements of the physical activity and the posture.

The above summary is not intended to describe each disclosed embodiment or every implementation of the present invention. The figures and detailed description that follow more particularly exemplify embodiments of the invention. While certain embodiments will be illustrated and described, the invention is not limited to use in such embodiments.

Figure 1:
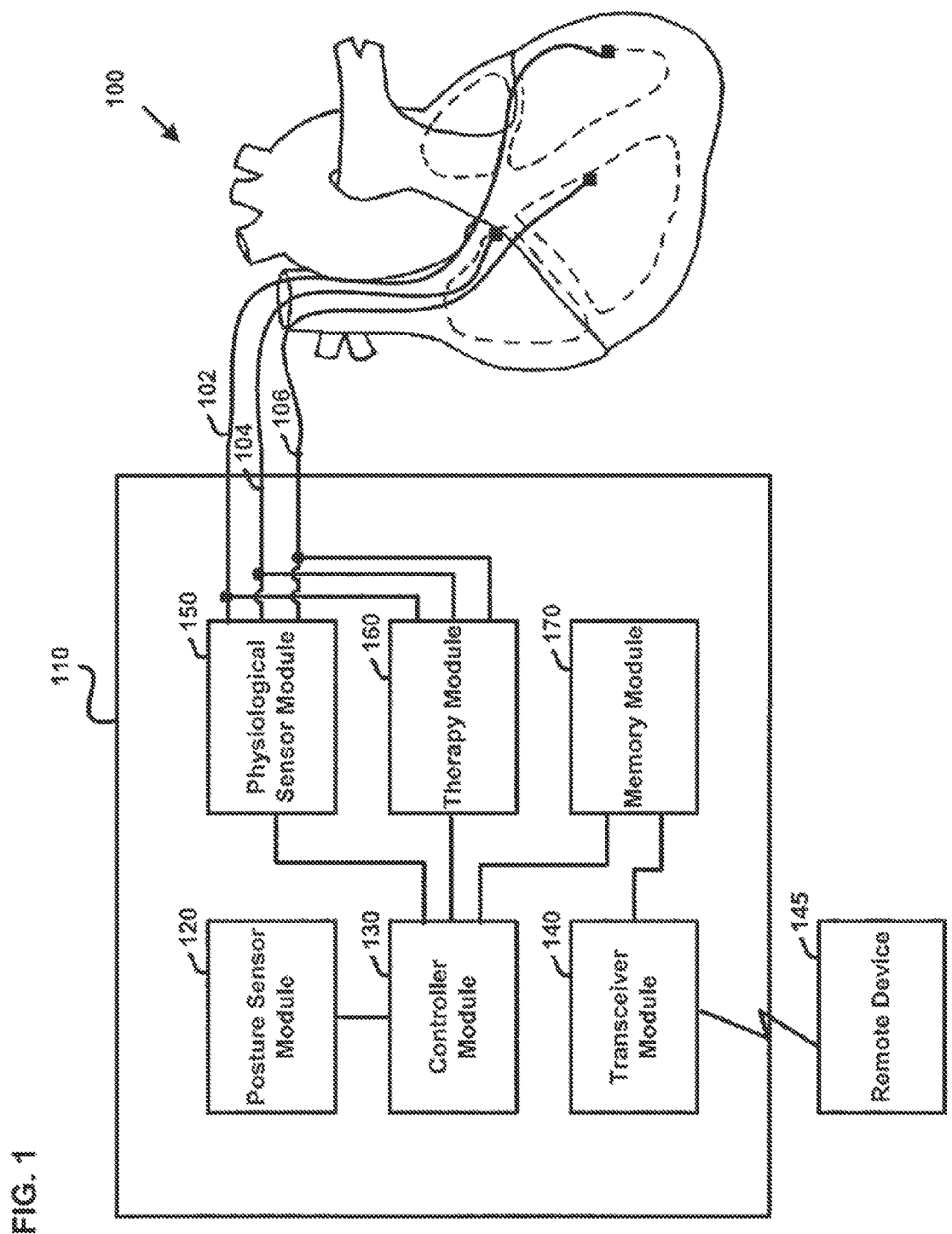
FIG. 1 is a schematic view of an example cardiac rhythm management device associated with a heart.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention relates to monitoring a patient's metabolic need over time and, more particularly, to estimating and tracking caloric expenditure using sensors associated with cardiac rhythm management devices.

Generally, systems and methods described herein are directed at the use of physiological data and posture data to estimate caloric expenditure. In example embodiments, posture data is used to validate and/or supplement caloric expenditure estimates.

For example, as described in more detail below, caloric expenditure can be estimated from physiological data measured by an accelerometer (XL) and/or minute ventilation (MV) sensor used in adaptive rate cardiac rhythm management devices implanted in patients using one or more of the methods described in U.S. Pat. No. 6,273,856 to Sun et al., filed Oct. 19, 1999 and entitled "Apparatus and Methods for METS Measurement by Accelerometer and Minute Ventilation Sensors," the entirety of which is hereby incorporated by reference.

Referring now to FIG. 1, a schematic representation of an example cardiac rhythm management device 110 is provided. The example device 110 has a plurality of logic units or modules, including a posture sensor module 120, controller 130, transceiver 140, physiological sensor module 150, therapy module 160, and memory module 170. The device 110 is associated with a patient's heart 100 through leads 102, 104, and 106.

The posture sensor module 120 is used to estimate a patient's posture (e.g., lying, sitting, standing, etc). There are several devices that can be used to measure a patient's posture. For example, U.S. Pat. No. 6,658,292 to Kroll et al., the entirety of which is hereby incorporated, discloses a three-dimensional accelerometer that can be used to estimate a patient's posture.

The controller module 130 controls the functioning of the device 110. For example, the controller module 130 can control the functioning of the posture sensor module 120.

The transceiver module 130 allows a remote device, such as remote device 145, to communicate with the device 110. For example, remote device 145 can be a programmer that communicates with device 110 using telemetry. In addition, remote device 145 can be an interrogator/transceiver unit that collects and forwards data from the device 110 to a central host as part of an advanced patient management system. See, for example, U.S. patent application Ser. No. 10/330,677 to Mazar et al., filed on Dec. 27, 2002, the entirety of which is hereby incorporated by reference.

The physiological sensor module 150 measures physiological data associated with the patient. For example, physiological sensor module 150 can be an accelerometer and/or a minute ventilation sensor, both of which are used, for example, in adaptive rate pacing. An accelerometer monitors an increase in acceleration as an individual moves, such as during walking or running, and equates the increase in acceleration with an increase in physical activity. A minute ventilation sensor monitors the breathing of the individual and equates increased respiration with increased physical activity. Specifically, a minute ventilation sensor can measure the volume of air inhaled and exhaled during a particular period of time, typically by measuring transthoracic impedance. Therefore, both the accelerometer and the minute ventilation sensor provide measurements that are indicative of a patient's physical activity level at a given point in time.

The therapy module 160 is used to deliver therapy to the patient. For example, the therapy module 160 can be configured to deliver pacing therapy, cardiac resynchronization therapy, and/or defibrillation therapy to the patient through one or more of leads 102, 104, and 106.

The memory module 170 stores data associated with the device 110. For example, the memory module 170 can store physiological data, as well as derived measurements such as caloric expenditure estimations. The data stored in memory module 170 can be accessed, for example, by remote device 145.

The modules associated with device 110 are examples only. Additional or different modules can also be provided as part of device 110. In addition, although example device 110 is an implanted device, other embodiments can include devices external to the patient's body. For example, in some embodiments, the physiological sensor module and/or the posture sensor module can be part of an external (i.e., non-implanted) device.

As described in U.S. Pat. No. 6,273,856, a cardiac rhythm management device having an accelerometer and/or a minute ventilation sensor, such as device 110 described above with reference to FIG. 1, when implanted in a patient, can gather data that can be used to estimate the caloric expenditure of a patient.

Caloric expenditure is typically expressed in terms of metabolic equivalents (METS), a unit of caloric expenditure defined in Equation A below, that are proportional to work load or oxygen uptake ($VO_2$).

$$1 \text{ METS} = 3.5 \text{ ml/(kg min)} \quad (A)$$

At rest, a person uses approximately 1 MET. Walking at 3 miles per hour, a person uses approximately 3.3 METS. Although METS are used herein as a unit of measure of caloric expenditure, other units representing the energy consumed by the body can also be used.

For example, the data collected by an accelerometer or minute ventilation sensor can be converted into METS using Equation B related to accelerometers (XL) and/or Equation C related to minute ventilation (MV) sensors, $$\text{XL METS} = 0.0576 \times \text{XL} + 1 \quad (B)$$

$$\text{MV METS} = 0.0172 \times \text{MV} + 1 \quad (C)$$

See U.S. Pat. No. 6,273,856 for additional details regarding Equations B and C.

Other sensors can also be used to estimate METS. For example, in chronotropically competent patients, activity level can be estimated based on intrinsic heart rate measured by the cardiac rhythm management device 110.

Using Equations B and/or C, a patient's caloric expenditure can be estimated based on data from an implanted accelerometer and/or minute ventilation sensor. However, data measured by an accelerometer and minute ventilation sensor can deviate from a patient's actual activity level in certain situations. For example, an accelerometer can sometimes pick up artifact associated with a patient's small movements while sitting, thereby providing an inaccurate estimate of a patient's activity level at a given time. In a similar manner, a minute ventilation sensor can inaccurately associate a patient's increased level of breathing due to a stressful event as an increased level of physical activity.

In example methods described herein, posture can be used to validate and/or supplement caloric expenditure estimates calculated using data from adaptive rate cardiac rhythm management devices such as accelerometers and minute ventilation sensors.

Figure 2:
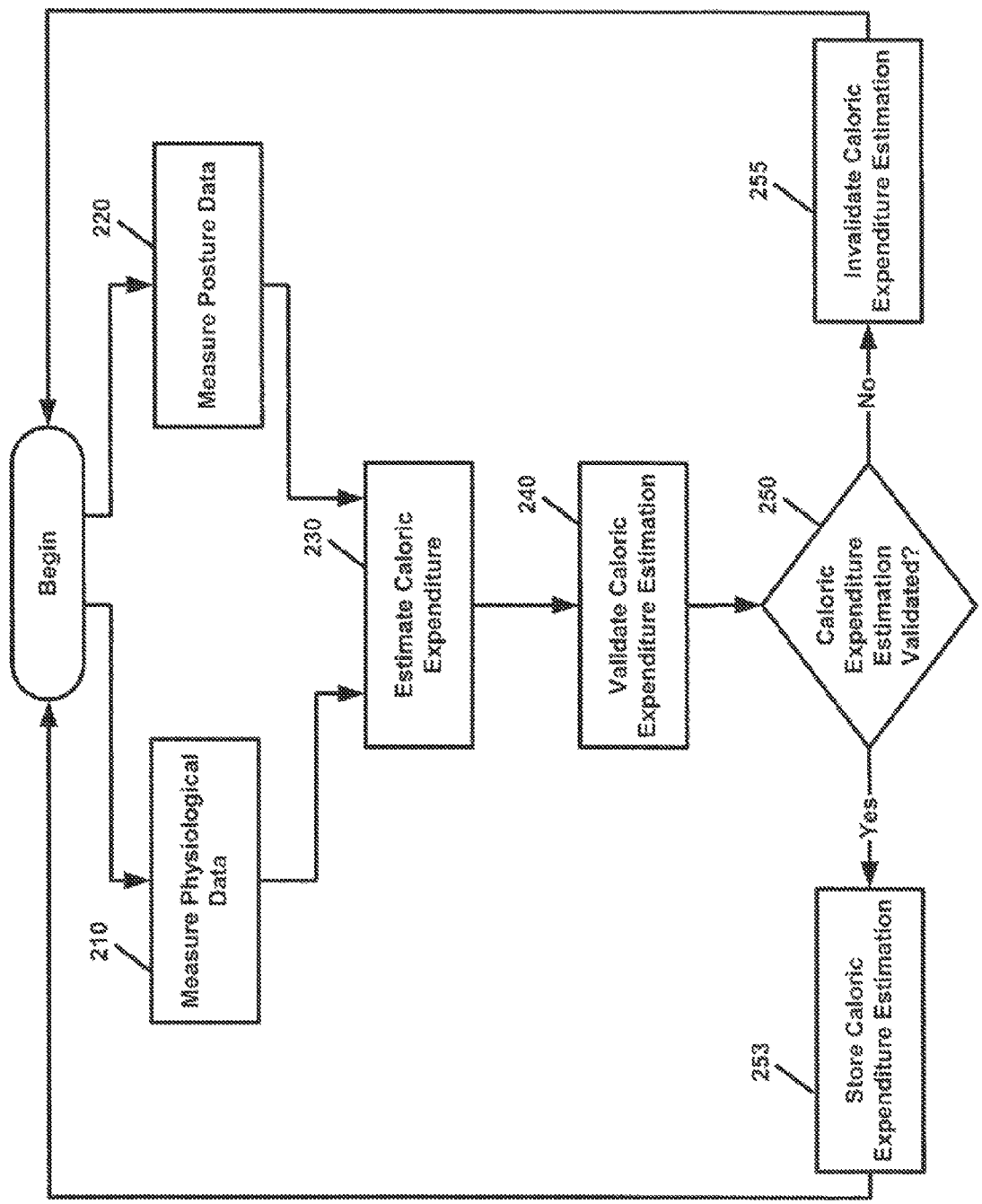
FIG. 2 is a flow diagram of an example method for estimating caloric expenditure using physiological data and posture data.

Referring now to FIG. 2, an example method for estimating a patient's caloric expenditure is illustrated. Generally, this method involves measurement of physiological data to estimate caloric expenditure, as well as use of posture data to validate the estimate.

At operation 210, physiological data associated with a patient's activity is measured. For example, as described above, a patient's activity level can be estimated using an accelerometer and/or a minute ventilation sensor associated with an implanted cardiac rhythm management device.

At operation 220, a patient's posture is estimated using, for example, a three-dimensional accelerometer. The patient's posture is measured at approximately the same time that the activity level measurement is made in operation 210.

Control is then passed to operation 230, wherein caloric expenditure is estimated based on the physiological data measured in operation 210. For example, caloric expenditure can be estimated by one of Equations B and C using data from a physiological sensor such as an accelerometer and/or minute ventilation sensor.

Next, in operation 240, the estimated caloric expenditure, typically expressed in terms of METS, is validated based on the estimate of posture made in operation 220. More specifically, as illustrated in Table 1 below, an expected MET level can be estimated based on an individual's posture.

TABLE 1

| Posture | Estimated METS |
|---|---|
| Lying Down | 1 |
| Sitting | 1-2 |
| Standing | 2 |
| Walking | 5 |
| Running | 8 |

For example, if a patient is lying down, a MET level of less than or equal to 1 MET is expected. The estimated MET levels in Table 1 can be preset based on expected values for a population, or the estimated MET levels can be individually set based on specific clinical data associated with a patient.

Referring back to operation 240 of FIG. 2, the estimated caloric expenditure of operation 230 is validated according to the posture measurements of operation 220. For example, if an estimated of 1 MET is calculated and the posture estimation is lying down, the estimated caloric expenditure (i.e., 1 MET) is validated according to the expected value provided in Table 1 (i.e., 1 MET) because the estimated caloric expenditure is less than or equal to the expected MET level based on the posture measurement. If the caloric expenditure is validated, control is passed to operation 253, where the measurement can be stored in memory for later use.

However, if the estimated MET level is not validated (i.e., the estimated MET level falls outside or exceeds the expected MET level provided in Table 1), control is passed to operation 255 and the caloric expenditure estimation in invalidated. In one example, if a specific caloric expenditure estimation is invalidated, the estimation is discarded. In another example, if a specific expenditure estimation is invalidated, the estimation is flagged as invalid, but the estimation is still stored in memory for later use.

Control is passed from operations 253 and 255 back to begin the process again at periodic intervals. For example, in some embodiments, caloric expenditure is estimated at intervals of hours or days. For example, in one embodiment, caloric expenditure is estimated each minute based on data collected by the physiological and posture sensors. In other embodiments, caloric expenditure can be estimated every hour, every few hours, or once a day. The caloric expenditure estimates are trended over time.

Figure 3:
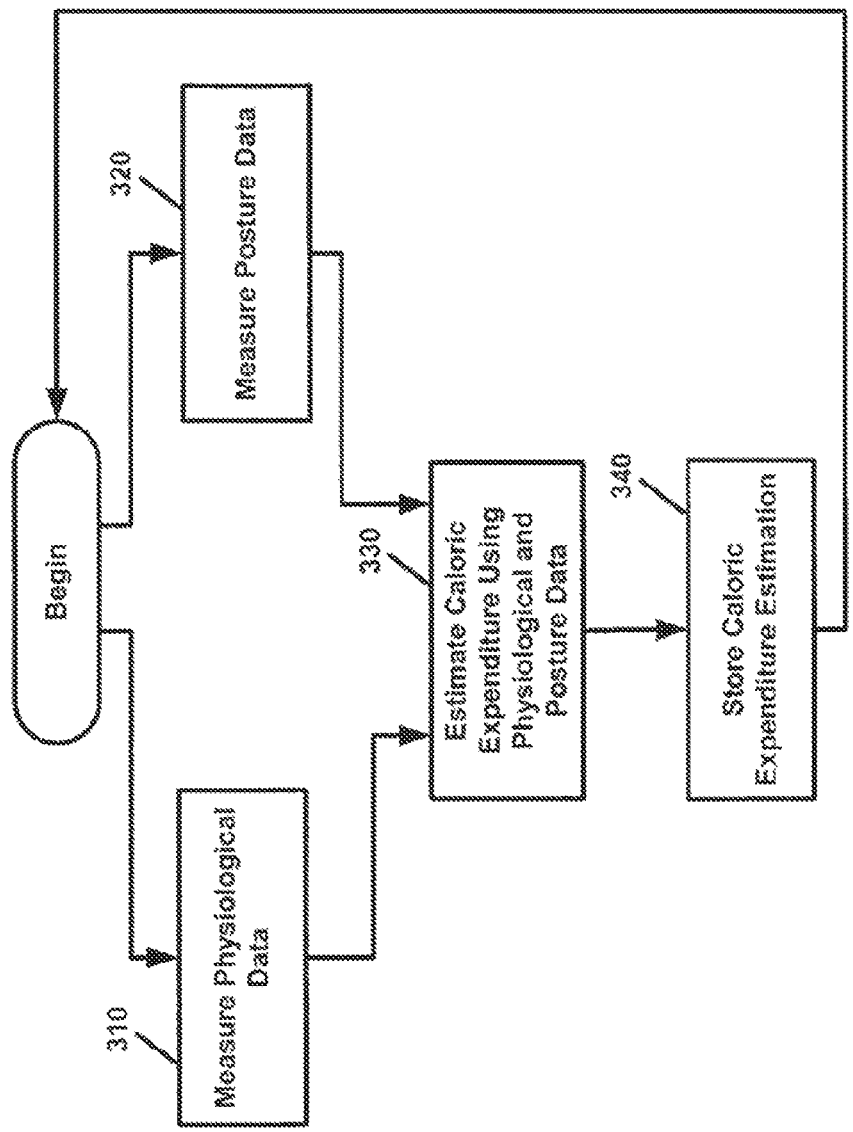
FIG. 3 is a flow diagram of another example method for estimating caloric expenditure using physiological data and posture data.

Referring now to FIG. 3, another example method for estimating a patient's caloric expenditure is illustrated. Generally, this method is similar to the method illustrated in FIG. 2, except that posture data is incorporated into the actual calculation of estimated caloric expenditure rather than being used to validate the estimate.

At operations 310 and 320, physiological data and posture data are measured. Next, in operation 330, caloric expenditure is estimated using the physiological and posture data. For example, equation D provides one example of how an estimated caloric expenditure value can be calculated using both physiological data and posture data.

$$METS = a \times XL + k \quad (D)$$

In Equation D, "XL" is the data associated with the physiological measurement, "k" is a constant, and "a" is one of multiple conversion factors associated with both (i) the type of sensor used to measure the physiological data (e.g., accelerometer or minute ventilation sensor and (ii) posture. Depending on the estimated posture; the conversion factor "a" can be increased or decreased. For example, the conversion factor "a" can be increased if posture data indicates a standing posture, while the conversion factor "a" can be decreased if the posture data indicates a lying down posture.

Equation D is provided as an example only, and conversion factors "a" and constant "k" can be empirically derived for a population and/or a given individual. Other equations estimating the relationship between caloric expenditure and physiological measurements and posture can also be used. For example, in other equations similar to Equation D, the posture data can be used as a constant rather than used to influence the magnitude of the conversion factor "a."

Finally, in operation 340 of FIG. 3, the caloric expenditure estimation is stored in memory for later use, and the process begins again.

The logical operations described herein can be implemented (1) as a sequence of computer implemented steps running on a computer system, and/or (2) as interconnected machine modules. This implementation is a matter of choice dependent on performance requirements. Accordingly, the logical operations making up the embodiments described herein are referred to as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

While the invention has been particularly shown and described with reference to preferred embodiments thereof, it will be understood by those skilled in the art that various other changes in the form and details may be made therein without departing from the spirit and scope of the invention.

What is claimed is:

1. A method for operating a cardiac rhythm management device to estimate caloric expenditure, comprising:
using a physiological sensor to produce electrical signals associated with a patient's physical activity;
using a posture sensor to produce electrical signals associated with the patient's posture; and,
operating a controller coupled to the physiological sensor and the posture sensor to:
determine a current posture of the patient from the posture sensor signals;
calculate an estimated caloric expenditure as a function of the electrical signals from the physiological sensor and the patient's posture, wherein caloric expenditure is defined as a number that corresponds to the amount of oxygen being consumed by the patient, by validating a first estimated caloric expenditure calculated as a function of electrical signals provided by the physiological sensor with a second estimated caloric expenditure calculated as a function of the patient's posture.

2. The method of claim 1 further comprising using the estimated caloric expenditure as a rate-controlling parameter for rate-adaptive pacing.

3. The method of claim 2 further comprising operating a transceiver to transmit the estimated caloric expenditure to an external device.

4. The method of claim 1 further comprising using an accelerometer as the posture sensor.

5. The method of claim 1 wherein the physiological sensor comprises one of a minute ventilation sensor and an accelerometer for measuring the physical activity.

6. The method of claim 1 further comprising operating the controller to store in a memory a historical trend of estimated caloric expenditures.

7. A cardiac rhythm management device, comprising:
a physiological sensor producing electrical signals associated with a patient's physical activity;
a posture sensor producing electrical signals associated with the patient's posture; and
a controller coupled to the physiological sensor and the posture sensor, the controller being configured to:
determine a current posture of the patient from the posture sensor signals;
calculate an estimated caloric expenditure as a function of the electrical signals from the physiological sensor and the patient's posture, wherein caloric expenditure is defined as a number that corresponds to the amount of oxygen being consumed by the patient, by validating a first estimated caloric expenditure calculated as a function of electrical signals provided by the physiological sensor with a second estimated caloric expenditure calculated as a function of the patient's posture.

8. The device of claim 7 wherein the physiological sensor includes an accelerometer.

9. The device of claim 7 wherein the physiological sensor includes a minute ventilation sensor.

10. The device of claim 7 wherein the device is an implanted cardiac rhythm management device.

11. The device of claim 10 wherein the device is a rate adaptive pacemaker, and wherein the estimated caloric expenditure comprises a rate controlling parameter for the rate adaptive pacemaker.

12. The device of claim 7 further comprising a memory to store a historical trend of previously calculated estimated caloric expenditures.

13. The device of claim 7 further comprising a transceiver module configured to communicate the estimated caloric expenditure to an external device.

* * * * *